(12) United States Patent
Kim et al.

(10) Patent No.: US 11,224,545 B2
(45) Date of Patent: Jan. 18, 2022

(54) SANITARY PAD FOR WOMEN

(71) Applicant: LEMON CO., LTD., Gyeongsangbuk-do (KR)

(72) Inventors: Hyo Gyu Kim, Seoul (KR); Kun Ho Ko, Jeju-do (KR); Dong Geun Kim, Daegu (KR); Jun Ho Cho, Gyeongsangbuk-do (KR)

(73) Assignee: LEMON CO., LTD., Gumi-si (KR)

( * ) Notice: Subject to any disclaimer, the term of this patent is extended or adjusted under 35 U.S.C. 154(b) by 470 days.

(21) Appl. No.: 16/283,271

(22) Filed: Feb. 22, 2019

(65) Prior Publication Data

US 2019/0282413 A1   Sep. 19, 2019

(30) Foreign Application Priority Data

Mar. 2, 2018  (KR) .................. 10-2018-0025385

(51) Int. Cl.
*A61F 13/514*     (2006.01)
*A61F 13/472*     (2006.01)
(Continued)

(52) U.S. Cl.
CPC ...... *A61F 13/472* (2013.01); *A61F 13/15203* (2013.01); *A61F 13/511* (2013.01); *A61F 13/514* (2013.01); *A61F 13/5148* (2013.01); *A61F 13/51458* (2013.01); *A61F 13/51462* (2013.01); *A61F 13/51478* (2013.01); *A61F 13/535* (2013.01); *A61F 13/53743* (2013.01); *B32B 5/022* (2013.01); *B32B 5/26* (2013.01); *D01D 5/003* (2013.01); *D01D 5/0007* (2013.01); *D01F 1/103* (2013.01); *D04H 1/728* (2013.01); *A61F 13/475* (2013.01); *A61F 2013/15373* (2013.01); *A61F 2013/15552* (2013.01); *A61F 2013/51409* (2013.01); *A61F 2013/51411* (2013.01); *A61F 2013/530007* (2013.01);
(Continued)

(58) Field of Classification Search
CPC .............. A61F 13/15203; A61F 13/472; A61F 13/51401; A61F 13/51458; A61F 13/51462; A61F 13/51478; A61F 2013/15373; A61F 2013/15552; A61F 2013/51409; A61F 2013/51411; A61F 2013/8414
See application file for complete search history.

(56) References Cited

U.S. PATENT DOCUMENTS

| 2012/0189534 | A1* | 7/2012 | Hussain | ............... C01G 5/00 |
| | | | | 423/604 |
| 2014/0272359 | A1* | 9/2014 | Cheng | ............... D04H 3/007 |
| | | | | 428/219 |
| 2017/0348165 | A1* | 12/2017 | Grenier | ............... A61F 13/539 |

FOREIGN PATENT DOCUMENTS

| KR | 1020040104276 | 12/2003 |
| KR | 1020050080166 | 8/2005 |

(Continued)

*Primary Examiner* — Catharine L Anderson
(74) *Attorney, Agent, or Firm* — Goldilocks Zone IP Law

(57) ABSTRACT

A sanitary napkin for women includes a permeable inner sheet, which comes into contact with the skin of a wearer to thus allow secretions to pass therethrough, an outer sheet fused to the inner sheet, and an absorption pad disposed between the inner sheet and the outer sheet to absorb the secretions passed through the inner sheet, the outer sheet being a nanolaminate film composed of a nanomembrane formed by electrospinning a polymer solution and a strength-reinforcing nonwoven fabric laminated on one side of the nanomembrane.

1 Claim, 4 Drawing Sheets

(51) Int. Cl.
   *A61F 13/15*    (2006.01)
   *A61F 13/511*   (2006.01)
   *A61F 13/535*   (2006.01)
   *A61F 13/537*   (2006.01)
   *B32B 5/26*     (2006.01)
   *D04H 1/728*    (2012.01)
   *D01D 5/00*     (2006.01)
   *B32B 5/02*     (2006.01)
   *D01F 1/10*     (2006.01)
   *A61F 13/475*       (2006.01)
   *A61F 13/53*        (2006.01)
   *A61F 13/534*       (2006.01)
   *A61F 13/84*        (2006.01)

(52) U.S. Cl.
   CPC .............. *A61F 2013/53445* (2013.01); *A61F 2013/8414* (2013.01)

(56) References Cited

FOREIGN PATENT DOCUMENTS

| | | |
|---|---|---|
| KR | 1020070058778 | 6/2007 |
| KR | 1020070073850 | 7/2007 |
| KR | 2020080004077 | 9/2008 |
| KR | 2020090010800 | 10/2009 |
| KR | 1020100099919 | 9/2010 |
| KR | 1020120003790 | 1/2012 |

\* cited by examiner

SANITARY PAD FOR WOMEN

BACKGROUND OF THE INVENTION

1. Technical Field

The present invention relates to a sanitary napkin for women, and more particularly to a sanitary napkin for women having superior waterproofness and air permeability.

2. Description of the Related Art

Generally, sanitary napkins are pads that are able to absorb women's secretions such as menstrual blood or leukorrhea, and are mainly responsible for absorbing liquid secretions and preventing them from leaking out.

In particular, since menstrual blood contains a cellulose component and a mucus substance, bacteria proliferate therein when sanitary napkins are used for a long period of time, thus causing offensive odors and various diseases.

The most important role of a sanitary napkin is to exhibit waterproofing with respect to the absorbed menstrual blood and to reduce moisture, which is the main cause of bacterial growth.

A typical sanitary napkin is configured to include an inner sheet, which comes into contact with the skin of a wearer to thus pass secretions therethrough, an impermeable outer sheet having the same size and shape as the inner sheet and fused to the inner sheet, an absorption pad interposed between the inner sheet and the outer sheet, and an adhesive part formed on the outer surface of the outer sheet so as to be attached to the underwear.

Additionally, a sanitary napkin having flaps (wings) configured to fold at the crotch portions of the underwear is widely used.

With such a typical sanitary napkin, however, when the inner sheet and the absorbent pad absorb secretions such as menstrual blood and the like, leakage may occur due to the spacing between a woman's intimate area and a sanitary napkin.

Therefore, the following related techniques have been devised to solve the leakage problem with sanitary napkins.

Patent Document 1 discloses a sanitary napkin, comprising a close-contactable absorption pad fixedly disposed in a longitudinal direction between an inner sheet and an absorption pad so that the surface of the inner sheet protrudes at a predetermined height to thus come into close contact with a woman's intimate area, and a nonwoven-fabric pad disposed between the close-contactable absorption pad and the inner sheet so that the absorbed secretions are quickly absorbed into the lower portion thereof.

Patent Document 2 discloses a sanitary napkin, the contact portion of which is convexly formed in the shape of a human body structure around a woman's intimate area (Y shape), and Patent Document 3 discloses a sanitary napkin configured such that an absorption pad interposed between an inner sheet and an outer sheet comprises a plurality of absorbent members, and adjacent absorbent members are spaced a predetermined interval apart from each other so as to form a flow passage connecting them to each other.

However, all of Patent Documents 1 to 3, which are focused on structural changes to the sanitary napkin, are problematic because of the poor fit and high manufacturing costs thereof, and also because, although waterproofness may be improved to some extent, problems related to air permeability are not solved at all due to the impermeable outer sheet.

The conventional sanitary napkins, which are able to prevent secretions from leaking out, do not take into consideration air permeability, and thus still cannot prevent rashes or bacterial growth caused by moisture and do not solve the problem of discomfort of the wearer.

SUMMARY OF THE INVENTION

Accordingly, the present invention has been made keeping in mind the problems encountered in the related art, and the present invention is intended to provide a sanitary napkin, which is capable of exhibiting waterproofness that prevents secretions such as menstrual blood and the like from leaking out and also superior air permeability so that a variety of bacteria may be prevented from growing due to moisture, as well as preventing rashes caused by moisture and eliminating the discomfort of a wearer.

The present applicant has accumulated technology pertaining to nanofiber through numerous studies and investment for many years, and the present applicant has recognized that the manufactured nanofiber may be applied to a sanitary napkin for women in view of the fact that the contact sensation of the nanofiber with the skin is excellent and air permeability is very high even though liquid is not capable of permeating the same, and thus actual products have been manufactured.

The present invention provides a sanitary napkin for women, comprising a permeable inner sheet, which comes into contact with the skin of a wearer to thus allow secretions to pass therethrough, an outer sheet fused to the inner sheet, and an absorption pad disposed between the inner sheet and the outer sheet to absorb the secretions passed through the inner sheet, the outer sheet being a nanolaminate film composed of a nanomembrane formed by electrospinning a polymer solution and a strength-reinforcing nonwoven fabric laminated on one side of the nanomembrane.

Here, the nanomembrane includes silver nanoparticles to thus be improved in antimicrobial activity by adding silver nitrate to the polymer solution for the preparation of nanofiber.

The nanomembrane and the strength-reinforcing nonwoven fabric are preferably adhered to each other using 4 to 16 $g/m^2$ of a moisture-curable hot-melt adhesive.

As such, the nanomembrane of the nanolaminate film preferably has a weight of 2.0 to 6.0 $g/m^2$, a thickness of 4.0 to 18.0 μm, and air permeability of 1.5 CFM or more at 125 Pa.

According to the present invention, a sanitary napkin is capable of ensuring air permeability through nano-sized pores while maintaining waterproofness, and is thus effective at preventing the growth of bacteria in a sanitary napkin and a woman's intimate area and is also thin and light, and provides an excellent contact sensation with the skin.

DETAILED DESCRIPTION OF THE INVENTION

Figure 1:
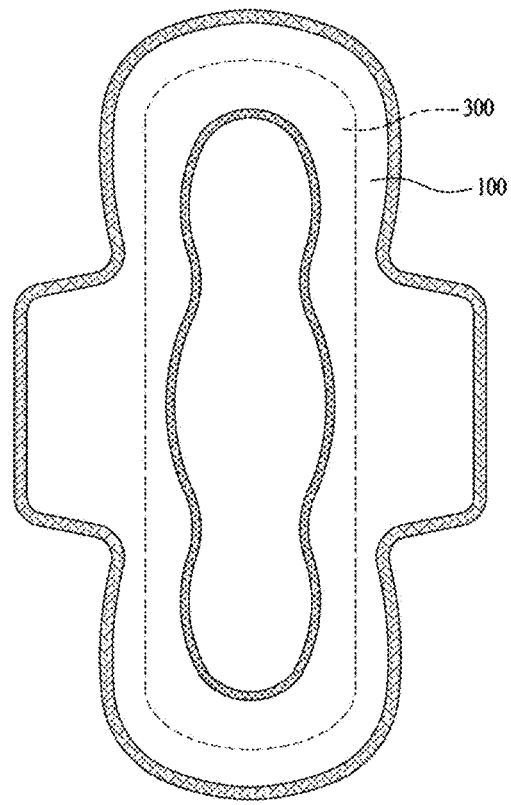
FIG. 1 is a top plan view showing the outer appearance of a sanitary napkin for women according to the present invention.
Figure 2:
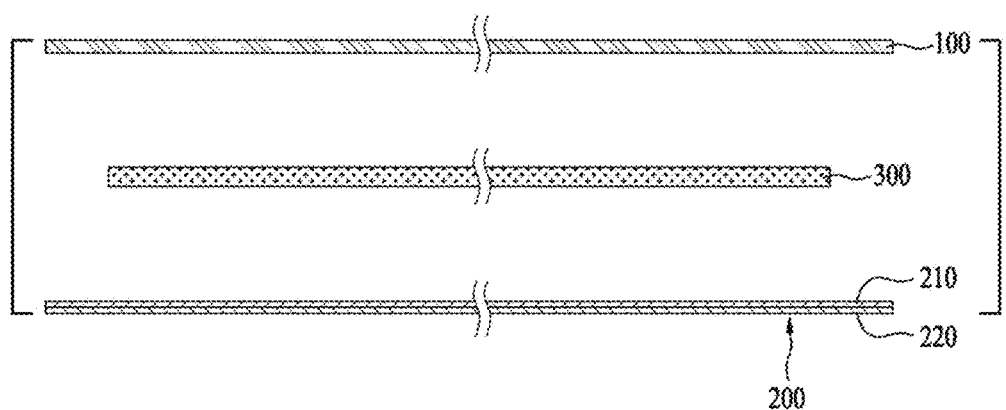
FIG. 2 is an exploded cross-sectional view showing the structure of FIG. 1.

FIG. 1 is a top plan view showing the outer appearance of a sanitary napkin for women according to the present invention, and FIG. 2 is an exploded cross-sectional view showing the structure of the sanitary napkin of FIG. 1.

As shown in FIG. 2, the sanitary napkin of FIG. 1 is configured to include a permeable inner sheet 100, which comes into contact with the skin of a wearer to thus allow secretions to pass therethrough, an outer sheet 200, fused at edges to the inner sheet 100, and an absorption pad 300, disposed between the inner sheet 100 and the outer sheet 200 to absorb the secretions passed through the inner sheet 100.

The inner sheet 100, which comes into contact with the skin of a wearer, is configured to absorb secretions such as menstrual blood and the like to thus pass therethrough, and is thus mainly formed of polyethylene or cotton, which is soft and has high permeability.

Also, the absorption pad 300, which absorbs and stores the secretions such as menstrual blood and the like, is disposed between the inner sheet 100 and the outer sheet 200, and is made of nonwoven fabric or pulp having high flexibility and liquid storage ability.

The inner sheet 100 and the absorption pad 300 are generally used and known, and a detailed description of materials or manufacturing methods thereof is thus omitted.

The main feature of the present invention is the outer sheet 200 in the configuration of FIGS. 1 and 2.

Figure 3:
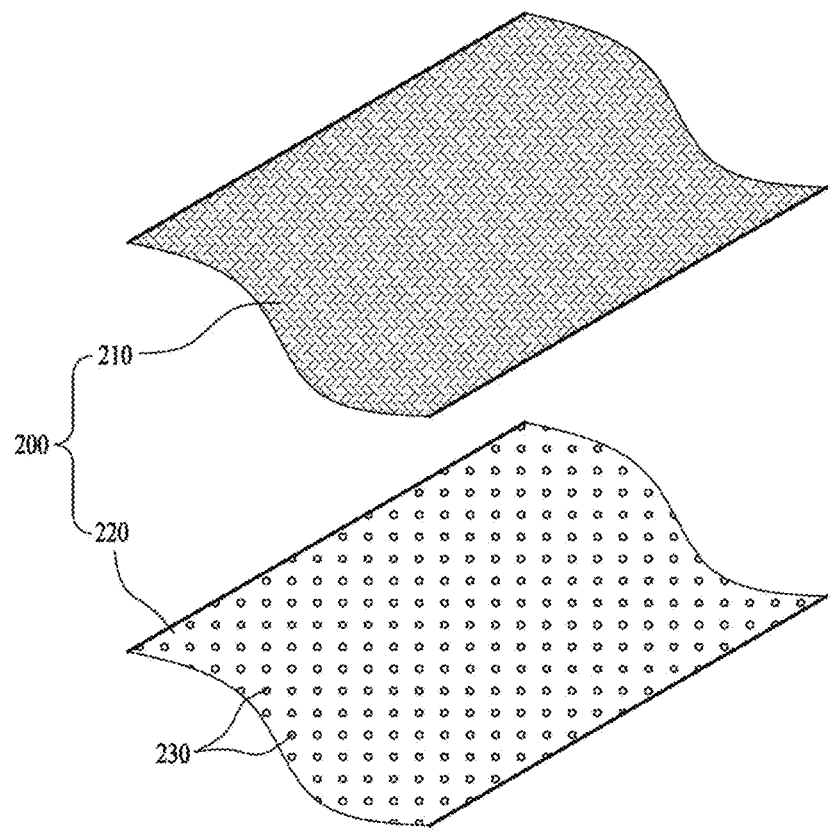
FIG. 3 is an exploded perspective view showing the structure of an outer sheet according to the present invention.

As shown in FIG. 3, the outer sheet 200 of the sanitary napkin for women according to the present invention comes into contact with the underwear such as panties, and the edges thereof are adhered to the inner sheet 100.

The outer sheet 200 is a nanolaminate film.

As illustrated in FIG. 3, the outer sheet 200 includes a nanomembrane 210, obtained by electrospinning a polymer solution, and a strength-reinforcing nonwoven fabric 220, laminated on one side of the nanomembrane 210, and the nanomembrane 210 and the strength-reinforcing nonwoven fabric 220 are laminated with each other by means of a hot-melt adhesive 230 that is cured under predetermined humidity.

As described above, when the nanolaminate film using nanofiber having electromagnetic-wave-shielding effects or an ion-permeable membrane is applied to the outer sheet 200 of the sanitary napkin for women by the present applicant, different and excellent effects, which have not been recognized conventionally, may be exhibited.

Hereinafter, the configuration of the outer sheet 200 of the sanitary napkin for women according to the present invention and the method of manufacturing the same (Preparation Example) are described in detail.

Preparation Example

1. Formation of Nanomembrane 210

A nanomembrane is manufactured by electrospinning an electrospinning solution comprising a dissolved polymer (a solution obtained by dissolving a polymer in a solvent at a weight ratio of 1:1) at room temperature at a flow rate of 0.02 to 0.05 ml/min using an electrospinning device under the conditions that a spinning part and a stacking part are spaced apart from each other at a distance of 10 to 30 cm and that the applied voltage is adjusted in the range of 10 to 55 kV.

The polymer for use in the preparation of nanofiber is selected from the group consisting of polyurethane (PU), polyacrylonitrile (PAN), polyvinylalcohol (PVA), nylon, polyvinylidene fluoride (PVdF), polyhydroxybutyrate (PHB), polyethersulfone (PES), polyetherimide (PEI), polycaprolactone (PCL), polylactic acid (PLA), poly-L-lactic acid (PLLA), and combinations thereof.

Also, the solvent for dissolving the above polymer in order to perform electrospinning is selected from the group consisting of DMA (dimethyl acetamide), DMF (N,N-dimethylformamide), NMP (N-methyl-2-pyrrolidinone), DMSO (dimethyl sulfoxide), THF (tetrahydrofuran), DMAc (dimethylacetamide), EC (ethylene carbonate), DEC (diethyl carbonate), DMC (dimethyl carbonate), EMC (ethyl methyl carbonate), PC (propylene carbonate), water, acetic acid, formic acid, chloroform, dichloromethane, acetone, ethanol, and combinations thereof.

Used in the outer sheet 200 of the sanitary napkin for women according to the present invention, the nanomembrane 210 includes silver nanoparticles, which are known to have strong antimicrobial activity.

The silver nanoparticles are contained in the nanomembrane by adding silver nitrate in a predetermined amount upon preparation of the polymer solution.

Silver nitrate is present in ionized forms such as silver ions and nitrate ions in the polymer solution, and nitrate ions are volatilized and the solution in which only the silver ions are present is electrospun.

2. Formation of Strength-Reinforcing Nonwoven Fabric 220

Used in the sanitary napkin for women according to the present invention, the outer sheet 200 is obtained by laminating a strength-reinforcing nonwoven fabric 220 on one side of a nanomembrane 210.

The strength-reinforcing nonwoven fabric 220 is provided in order to reinforce the nanomembrane 210 because the nanomembrane 210 configured to allow only air, but not liquid, to pass therethrough is vulnerable to tearing.

The strength-reinforcing nonwoven fabric 220 is made of PP, PE, PET, etc.

In the present embodiment, a strength-reinforcing nonwoven fabric for use in the nanolaminate film of the outer sheet 220 is manufactured through a spun-bond process using polypropylene (PP).

PP pellets are sequentially placed in a water bath, a hopper and a screw extruder.

Extruder sleeve partition heating, melting with a continuous prefilter, slicing using an extruder and rotating in a rotary box are performed.

Accurate measurement using a metering pump, quantitative introduction of a melt using a spinning nozzle, and continuous melt flow through spraying using the openings of the nozzle are performed, thus forming raw fiber.

The raw fiber is absorbed by a monomer, followed by cooling using cold air, air drafting, and filament formation. The filament is uniformly perforated through a pendulum roller, is sent to a hot-rolling machine by a conveyor curtain using air flows having positive and negative pressure, and is evenly laid on a net curtain that forms a spun sticky web through heat bonding by the hot-rolling machine.

3. Hot-Melt Adhesive

The outer sheet 200 of the present invention is configured such that the nanomembrane 210 and the strength-reinforcing nonwoven fabric 220 are adhered to each other by means of the hot-melt adhesive.

The hot-melt adhesive is an adhesive which is thermoplastic, which is changed into a liquid phase by heat, and which has a characteristic of curing at a humidity of 80% or higher, and an acrylic resin may be used.

The solid adhesive is heated to a liquid phase and applied onto the surface of an engraved roller to thus be applied onto one side of the strength-reinforcing nonwoven fabric 220.

The hot-melt adhesive is applied in dot or line form onto one side of the strength-reinforcing nonwoven fabric 220, and the nanomembrane 210 is laminated thereon and then pressed.

Examples of a process of applying the hot-melt adhesive onto the surface of the strength-reinforcing nonwoven fabric may include a spraying process, a roller process and a blanket transformation process, but no particular limitation is imposed thereon, so long as the inherent functions of the nanomembrane are not damaged after bonding.

The weight of the adhesive that is transferred to the nonwoven fabric varies depending on the kind of nonwoven fabric. Preferably, the adhesive is used in an amount of about 4 to 10 $g/m^2$ for a nonwoven fabric having a flat surface, and is used in an amount of about 16 $g/m^2$ for a nonwoven fabric having a rough surface.

Accordingly, the weight of the hot-melt adhesive applied on the nonwoven fabric falls in the range of 4 to 16 $g/m^2$.

If the weight of the hot-melt adhesive is less than 4 $g/m^2$, adhesion of the nanomembrane 210 and the strength-reinforcing nonwoven fabric 220 may decrease and thus the nanomembrane 210 and the strength-reinforcing nonwoven fabric 220 are liable to separate from each other. On the other hand, if the weight thereof exceeds 16 $g/m^2$, air permeability may decrease, the total weight of the nanolaminate film may increase, and the adhesive may leak out.

Hence, it is important that the weight of the adhesive fall within the above numerical range.

4. Formation of Nanolaminate Film

A nanolaminate film is manufactured by engaging and rotating a first roller, on which the nanomembrane is wound, a second roller, on which the strength-reinforcing nonwoven fabric is wound, and an engraved roller, which rotates together with the second roller in contact therewith, followed by pressing.

Specifically, a hot-melt adhesive is melted at a temperature of about 1900 in an extruder, and is then applied onto the surface of an engraved roller. Here, the adhesive is applied at a uniform thickness on the surface of the engraved roller by means of a blade.

Thereafter, a strength-reinforcing nonwoven fabric is placed between the engraved roller and the second roller, whereby the adhesive applied on the engraved roller is transferred to the surface of the strength-reinforcing nonwoven fabric, and the nonwoven fabric on which the adhesive was applied is laminated with the nanomembrane fed from the first roller, and then passes through a pressing roller, thereby completing a nanolaminate film.

The engraved roller functions to press the strength-reinforcing nonwoven fabric at a pressure of 3 to 5 $kg/cm^2$, and the surface of the engraved roller is maintained at a temperature of 1900.

Experimental Example

The outer sheet 200 of a sanitary napkin for women according to the present embodiment was manufactured as described in the above Preparation Example, and the unit weight, thickness, air permeability and waterproofness thereof were measured under the following experimental conditions. As the Comparative Example, the outer sheets of commercially available sanitary napkins for women were tested under the same experimental conditions.

1. Weight of Nanomembrane

The weight of the outer sheet 200 of a sanitary napkin for women is the main factor that determines the fit with a wearer. The lighter the outer sheet, the better the fit.

A test sample was manufactured in a rectangular shape having a width of 250 mm and a length of 200 mm, and the weight thereof was measured in accordance with ASTM D 3886, and is represented in units of $g/m^2$.

Figure 4A:
FIG. 4A is photographs showing the measuring device of the unit weight of a nanomembrane according to the present invention.
Figure 4B:
FIG. 4B photographs showing the measurement result of the unit weight of a nanomembrane according to the present invention.

FIG. 4A shows photographs of the measuring device of the unit weight and FIG. 4B shows photographs captured during the measurement of the unit weight.

2. Thickness of Nanomembrane

The thickness of a nanomembrane was measured in accordance with ASTM D 1777, and is represented in units of μm. When the thickness is thinner to 100% point or more, effects are regarded as excellent.

Figure 5A:
FIG. 5A is photographs showing the measuring device of the thickness of the nanomembrane according to the present invention.

FIG. 5A shows photographs of the measuring device of the thickness of the outer sheet.

Figure 5B:
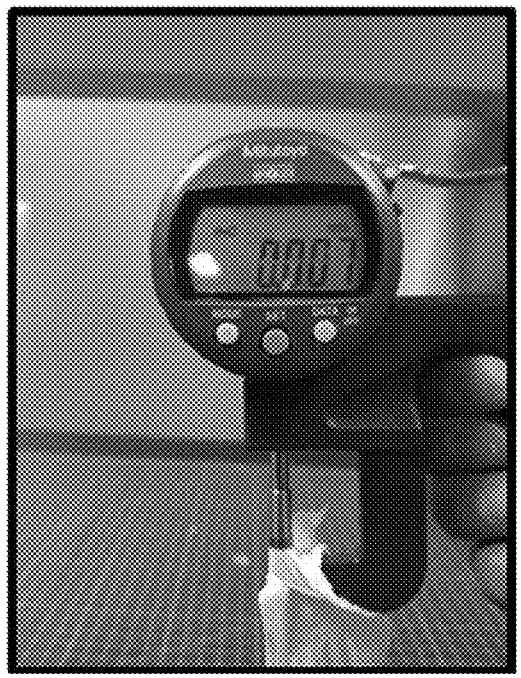
FIG. 5B is photographs showing the measurement result of the thickness of the nanomembrane according to the present invention.

FIG. 5B shows photographs captured during the measurement of the thickness of the outer sheet.

3. Measurement of Air Permeability of Nanolaminate Film

Air permeability was measured in accordance with ASTM D 737-04 (2008).

As such, the air permeability of the nanolaminate film comprising the nanomembrane and the strength-reinforcing nonwoven fabric, which were laminated together, was directly measured.

The strength-reinforcing nonwoven fabric has no effect on air permeability because the pore size of the nanomembrane is hundreds of times larger.

A sample was spread on an air permeability meter (Textest FX 3300), and was then fixed by pressing down a circular chamber having a diameter of 15 cm.

The set pressure was 125 Pa and the measured value was CFM (Cubic Feet per Minute). Briefly, the set pressure wad applied to the product and the amount of air passed through the sample was measured. The values at three diagonally distributed points for one sample were measured, and were then averaged.

Here, the weight of the nanomembrane according to the present invention was 4.0 g/m$^2$, and the thickness thereof was 7.0 μm, and air permeability was determined by measuring the amount of air passing therethrough using a flow meter at an air pressure of 125 Pa.

4. Measurement of Waterproofness (Water Repellency) of Nanolaminate Film

Waterproofness (water repellency) was measured in accordance with JIS L 1092 (2009).

A sample was cut into a square shape having a width and length of 200 mm each, placed on a holder with a diameter of 11.5 cm, fixed with a frame, and then pressurized.

Here, the nanolaminate film was disposed such that the surface thereof contacting water was a nanomembrane and the surface opposite thereto was a strength-reinforcing nonwoven fabric.

The water pressure was slowly increased while applying water pressure. While the water pressure was increased, the pressure at which the third droplet, among droplets, emerged from the gap in the outer sheet was measured.

When a third droplet was not observed even at a water pressure of 5000 mmH$_2$O, waterproofness was judged not to be problematic, and no further measurements were made.

Figure 6A:
FIG. 6A is photographs showing the measuring device of the waterproofness of a sanitary napkin for women according to the present invention.

FIG. 6A is photographs showing the measuring device of waterproofness of the nanolaminate.

Figure 6B:
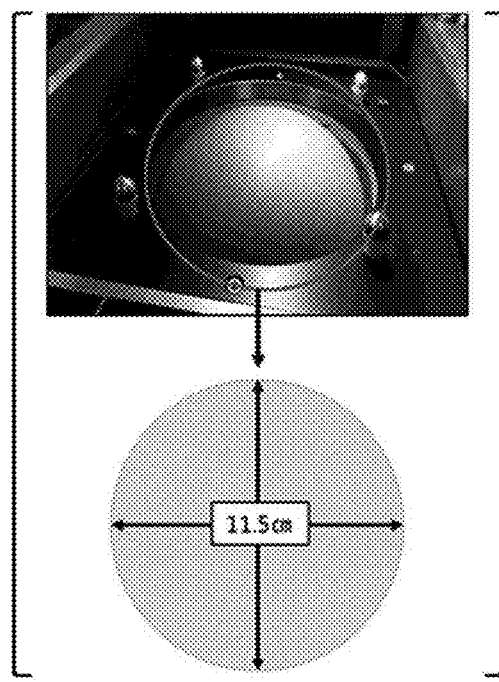
FIG. 6B is photographs showing the specifications of sample for measuring of the waterproofness of a sanitary napkin for women according to the present invention.

FIG. 6B is photographs showing the state (specification) of sample for measuring waterproofness.

5. Experimental Results (Comparative Example)

TABLE 1

|  | Unit | LEMON | A Company | B Company | C Company | D Company | E Company |
| --- | --- | --- | --- | --- | --- | --- | --- |
| Thickness | μm | 8 | 34 | 62 | 78 | 98 | 150 |
| Basis Weight | g/m$^2$ | 4.0 | 33 | 60 | 80 | 100 | 130 |
| Air permeability | CFM, @125 pa | 2.0 | 0.0001 | 0.0001 | 0.0001 | 0.0001 | 0.0001 |
| Water repellency | mmH$_2$O | 5,000↑ | 5,000↑ | 5,000↑ | 5,000↑ | 5,000↑ | 5,000↑ |

As is apparent from the above experimental results, the thickness of the nanomembrane used in the present invention is only 5.3% to 23.5% of that of the outer sheet of each of the commercially available sanitary napkins, the basis weight thereof is 3.0% to 12%, and the air permeability is as high as twenty thousand times thereof.

Figure 7:
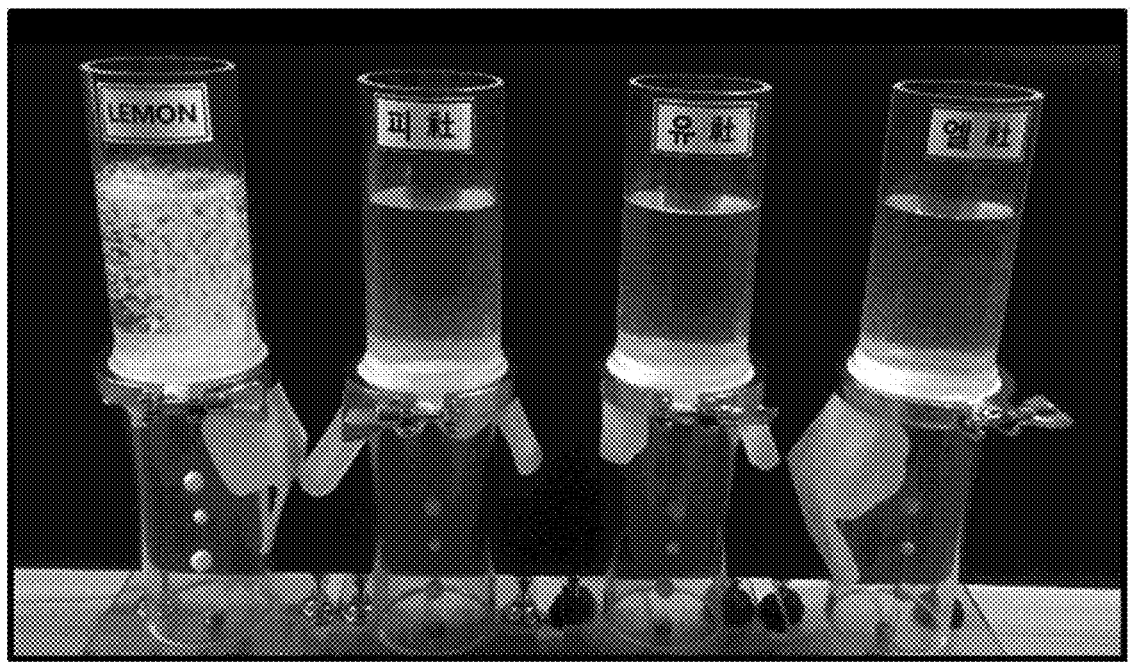
FIG. 7 is a comparison photograph for confirming the air permeability of the sanitary napkin for women according to the present invention.

Particularly, an experiment that may actually confirm air permeability along with waterproofness was performed as shown in FIG. 7.

FIG. 7 shows an actual testing photograph of a finished product of the sanitary napkin for women according to the present invention and commercially available sanitary napkins.

Specifically, as shown in the photograph of FIG. 7, for the sanitary napkin of the present invention, tested in a manner in which water was positioned on the top of the outer sheet and air was blown from the bottom thereof, it was confirmed that air bubbles were formed while the air from the bottom passed through the outer sheet and proceeded to the top without water leaking at all, whereas all of the remaining sanitary napkins were thus confirmed to have no air permeability because no air bubbles were formed.

If the weight of the nanomembrane exceeds 6.0 g/m$^2$ and the thickness of the nanomembrane exceeds 18.0 m, waterproofness is relatively improved, but air permeability is considerably lowered, which leads to discomfort in wearing and inconvenience due to the weight.

In the experiment of the present application, the air permeability of the nanomembrane having a weight of 7.0 g/m$^2$ and a thickness of 20 m was measured to be 0.7 CFM, which is regarded as a numerical value having a critical meaning taking into consideration that the air permeability of the nanomembrane having a weight of 6.0 g/m$^2$ and a thickness of 18.0 m was 1.5 CFM.

On the other hand, if the weight of the nanomembrane is less than 2.0 g/m$^2$ and the thickness of the nanomembrane is less than 4.0 m, air permeability is improved and thus the alleviation of rash and the fit are observed to improve, but a large number of droplets are formed within about 5 sec from the start of the experiment, waterproofness being measured to be about 500 to 1000 mmH$_2$O.

In the case of a nanomembrane having a weight less than 2.0 g/m$^2$ and a thickness less than 4.0 μm, leakage may occur in the sanitary napkin, on which basis it is judged that the same is not usable as a product.

Although the sanitary napkin for women according to the present invention has been described in the preferred embodiments, it is intended to facilitate understanding of the present invention and is not intended to limit the scope of the invention.

It will be understood by those skilled in the art that various changes and modifications may be made without departing from the scope of the invention.

What is claimed is:

1. A sanitary napkin for women, comprising: a permeable inner sheet, which comes into contact with skin of a wearer to thus allow secretions to pass therethrough; an outer sheet fused to the inner sheet; an absorption pad disposed between the inner sheet and the outer sheet to absorb the secretions passed through the inner sheet, wherein the outer sheet is a nanolaminate film composed of a nanomembrane formed by electrospinning a polymer solution and a strength-reinforcing nonwoven fabric laminated on one side of the nanomembrane, and the nanomembrane of the nanolaminate film has a weight of 2.0 g/m$^2$ to 6.0 g/m$^2$, a thickness of 4.0 m to 18.0 μm, and air permeability of 1.5 CFM or more at 125 Pa, wherein the nanomembrane and the strength-reinforcing nonwoven fabric are adhered to each other using 4.0 to 16 g/m2 of a moisture-curable hot-melt adhesive.

* * * * *